United States Patent
Kim et al.

(10) Patent No.: US 10,889,535 B2
(45) Date of Patent: Jan. 12, 2021

(54) PROCESS AND APPARATUS FOR SEPARATING ETHYLENE

(71) Applicant: LG CHEM, LTD., Seoul (KR)

(72) Inventors: Tae Woo Kim, Daejeon (KR); Sung Kyu Lee, Daejeon (KR); Joon Ho Shin, Daejeon (KR); Yeonuk Choo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/613,752

(22) PCT Filed: Nov. 21, 2017

(86) PCT No.: PCT/KR2017/013234
§ 371 (c)(1),
(2) Date: Nov. 14, 2019

(87) PCT Pub. No.: WO2018/225908
PCT Pub. Date: Dec. 13, 2018

(65) Prior Publication Data
US 2020/0071244 A1   Mar. 5, 2020

(30) Foreign Application Priority Data
Jun. 8, 2017   (KR) .................. 10-2017-0071315

(51) Int. Cl.
*C07C 5/08*   (2006.01)
*C07C 7/04*   (2006.01)
(52) U.S. Cl.
CPC .  *C07C 5/08* (2013.01); *C07C 7/04* (2013.01)

(58) Field of Classification Search
CPC .... C07C 5/08; C07C 7/04; C07C 7/00; C07C 7/005
See application file for complete search history.

(56) References Cited

U.S. PATENT DOCUMENTS

| | | | |
|---|---|---|---|
| 5,453,559 A * | 9/1995 | Phillips | C10G 5/04 585/809 |
| 5,884,504 A | 3/1999 | Nazar | |
| 7,207,192 B2 | 4/2007 | Ronczy | |
| 2006/0021379 A1 * | 2/2006 | Ronczy | F25J 3/0238 62/620 |
| 2016/0319206 A1 * | 11/2016 | Fritz | C07C 7/005 |

FOREIGN PATENT DOCUMENTS

| | | |
|---|---|---|
| CN | 102267850 A | 12/2011 |
| CN | 103664453 A | 3/2014 |
| JP | 3489158 B2 | 1/2004 |
| KR | 10-0338407 B1 | 5/2002 |
| KR | 10-2008-0056104 A | 6/2006 |
| KR | 10-1497692 B1 | 3/2015 |
| KR | 10-2016-0085851 A | 7/2016 |

* cited by examiner

Primary Examiner — Youngsul Jeong
(74) Attorney, Agent, or Firm — Dentons US LLP

(57) ABSTRACT

The present invention provides an ethylene separation process comprising an first and second deethanizer columns and an acetylene converter, thereby providing an ethylene stream having a purity of 99 wt % or more to the middle of an ethylene separation column. The present invention increases the production amount of ethylene and also reduces energy consumption by passing the feed through a preliminary ethylene separation process, without having to change existing facilities in which an acetylene converter is provided downstream of the deethanizer column.

7 Claims, 10 Drawing Sheets

RELATED ART
Fig. 1]
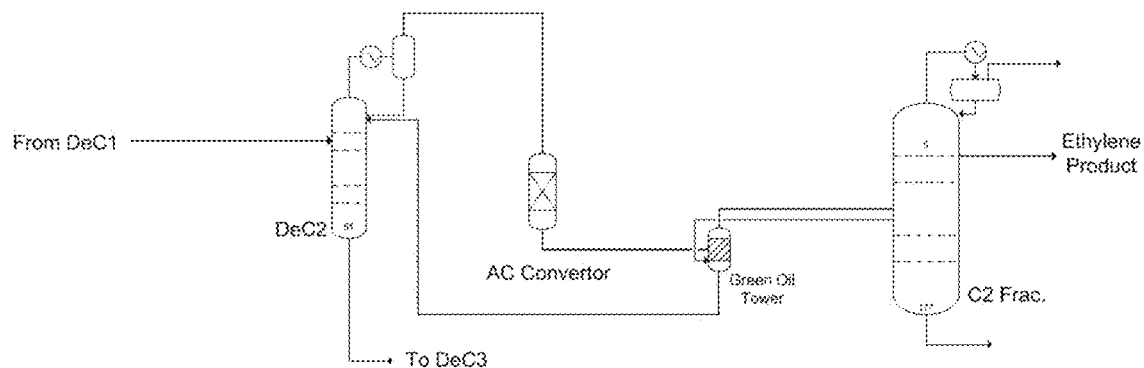

[Fig. 2]
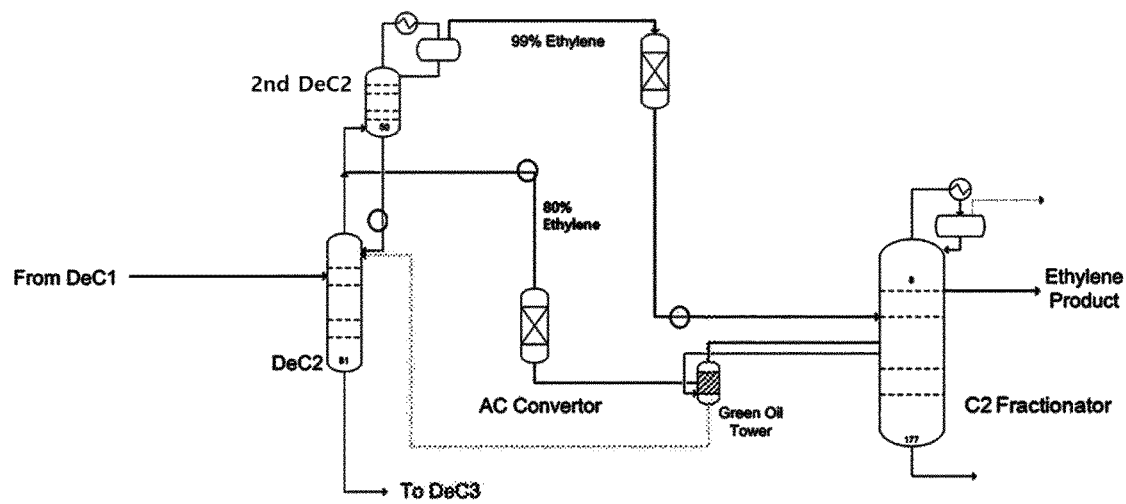

[Fig. 3]
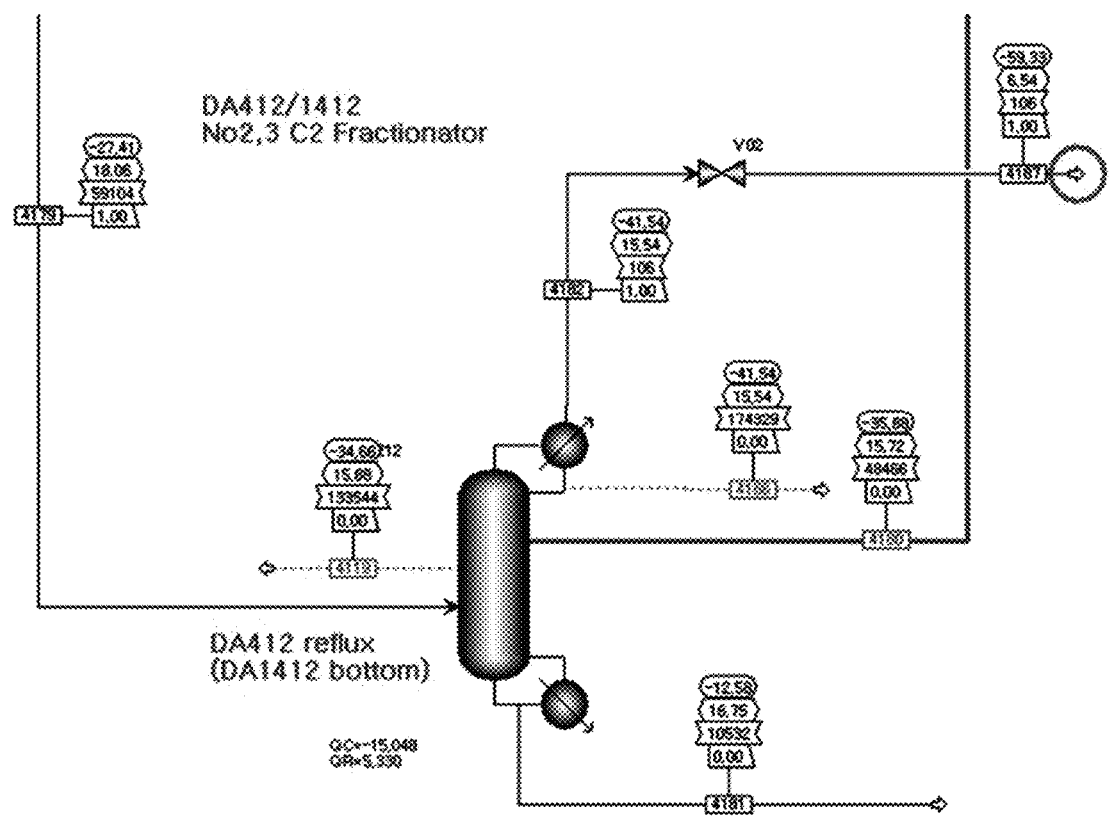

[Fig. 4]
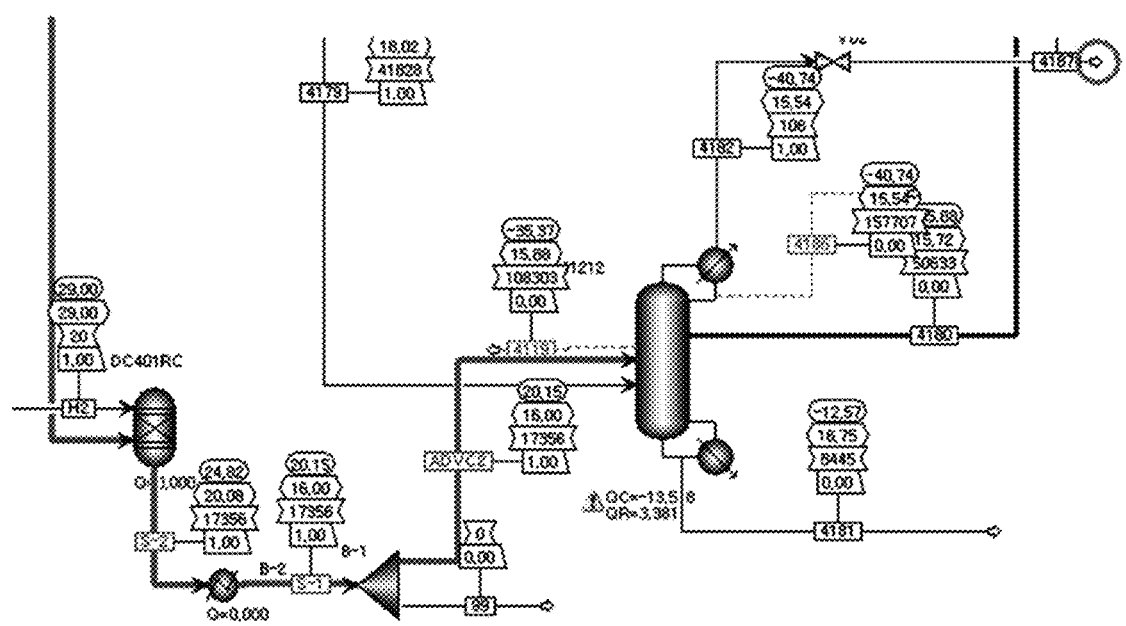

[Fig. 5]
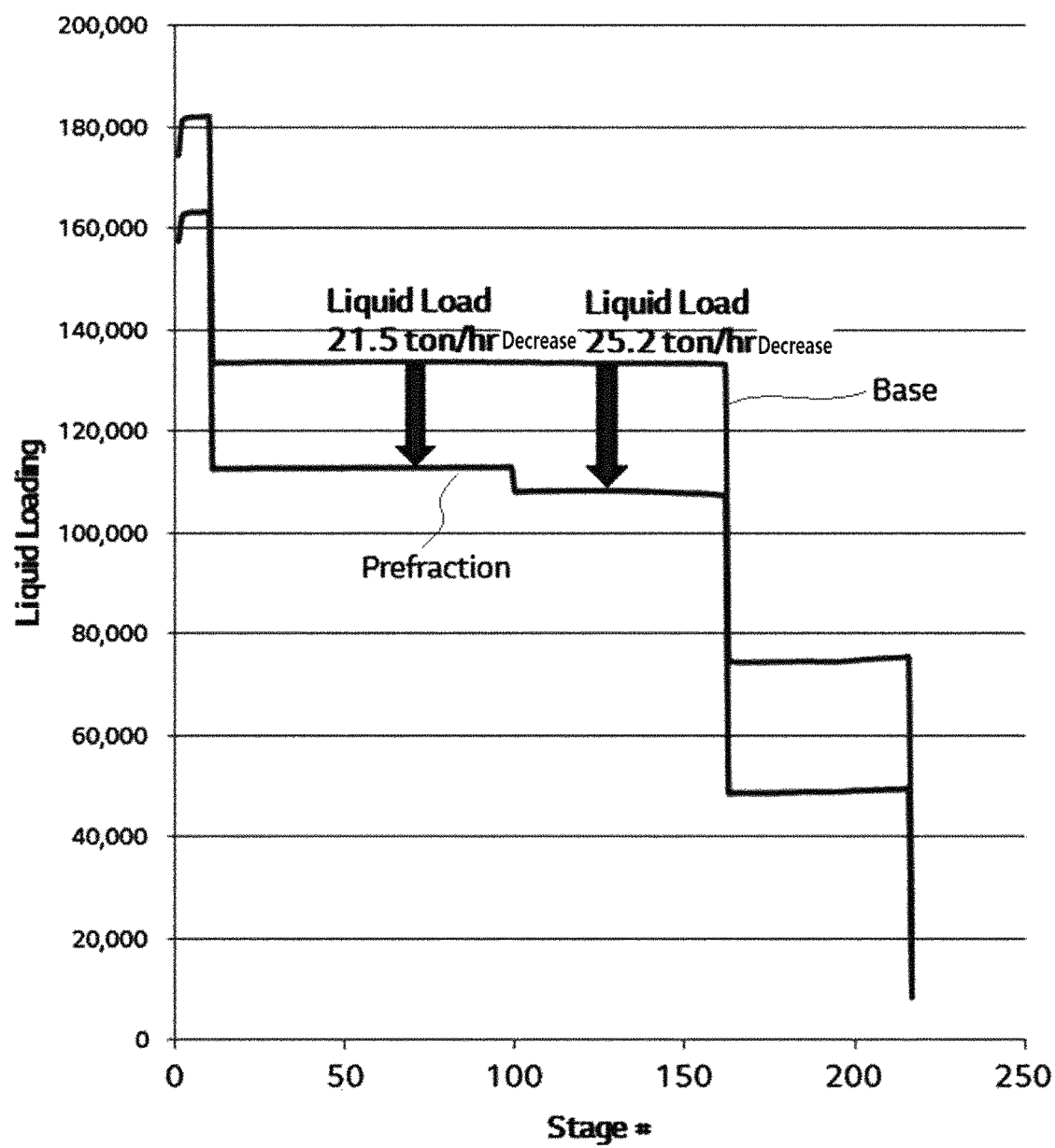

[Fig. 6]
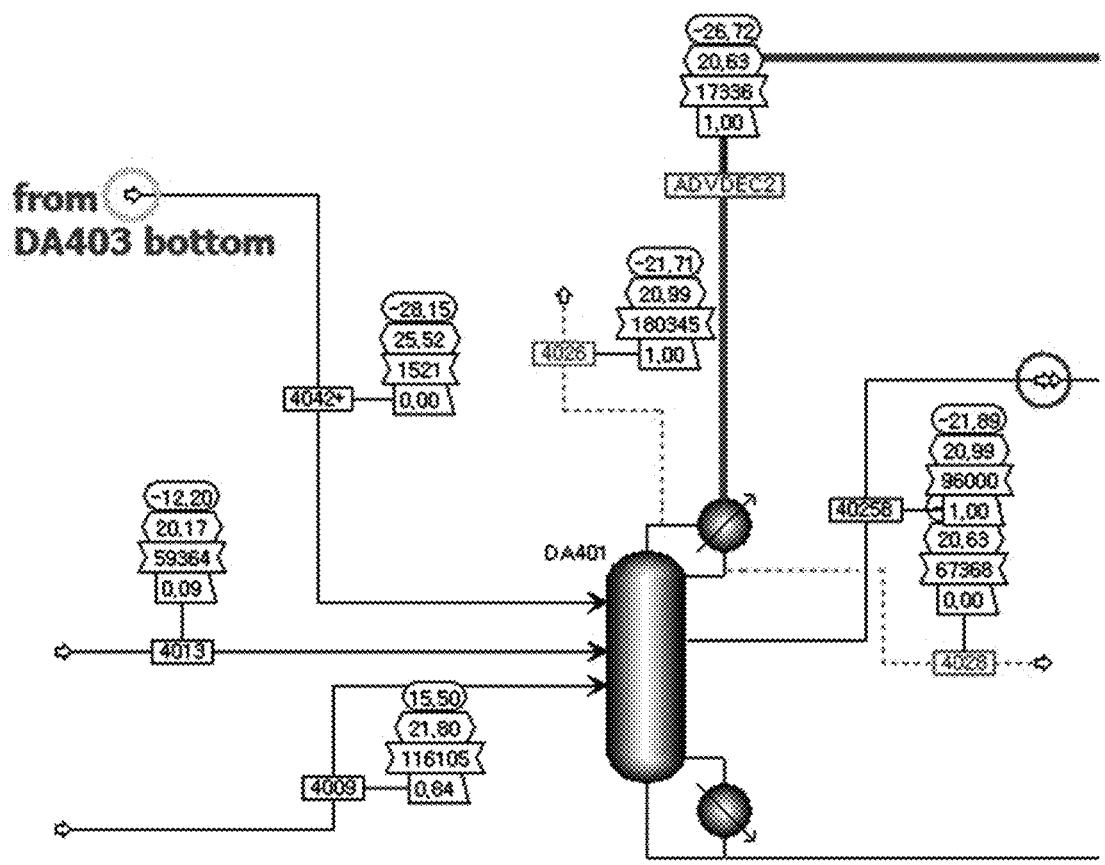

[Fig. 7]
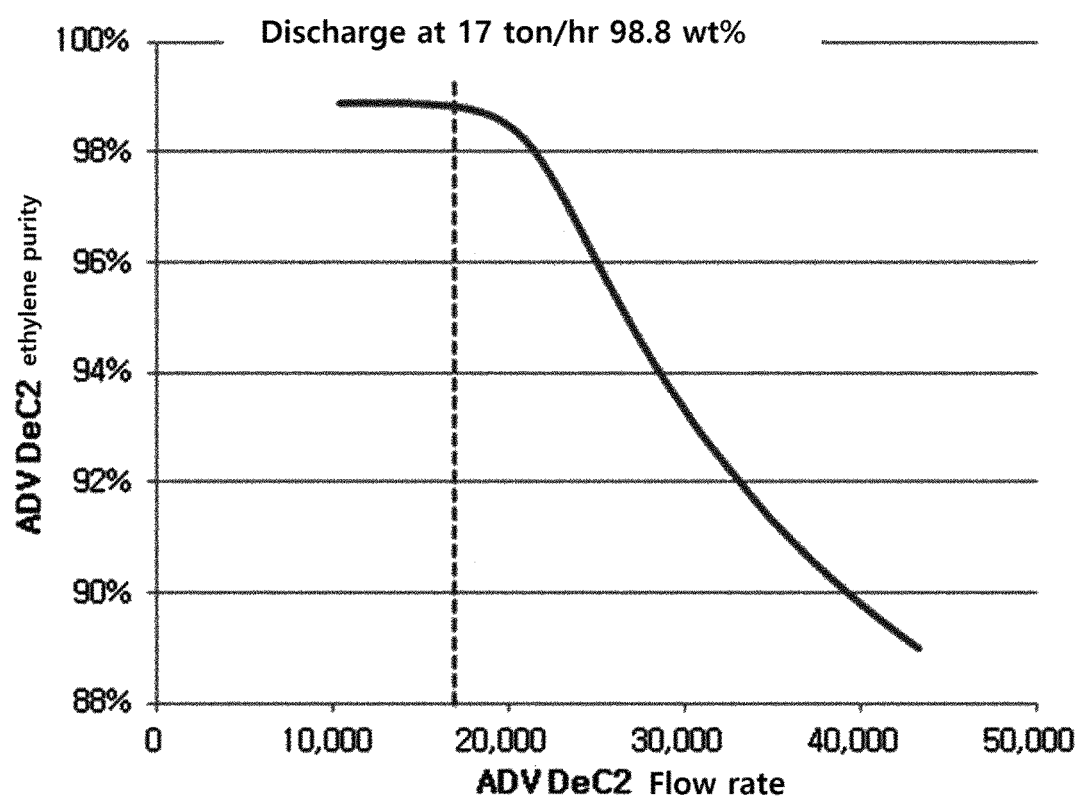

[Fig. 8]
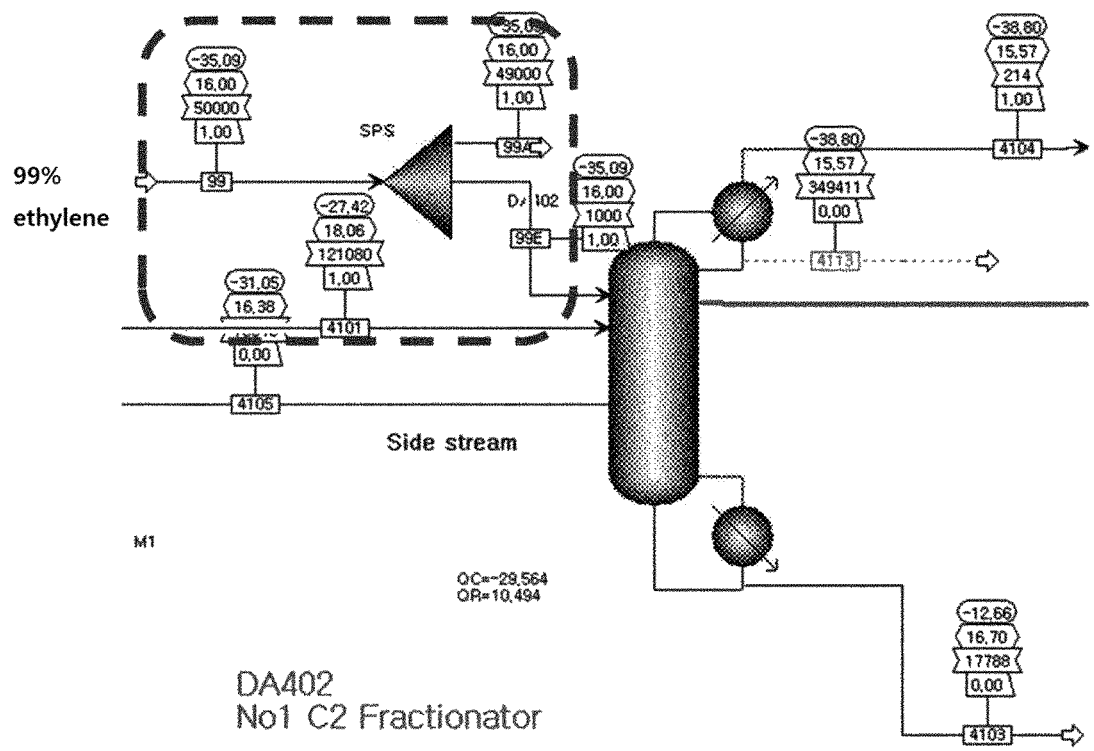

[Fig. 9]
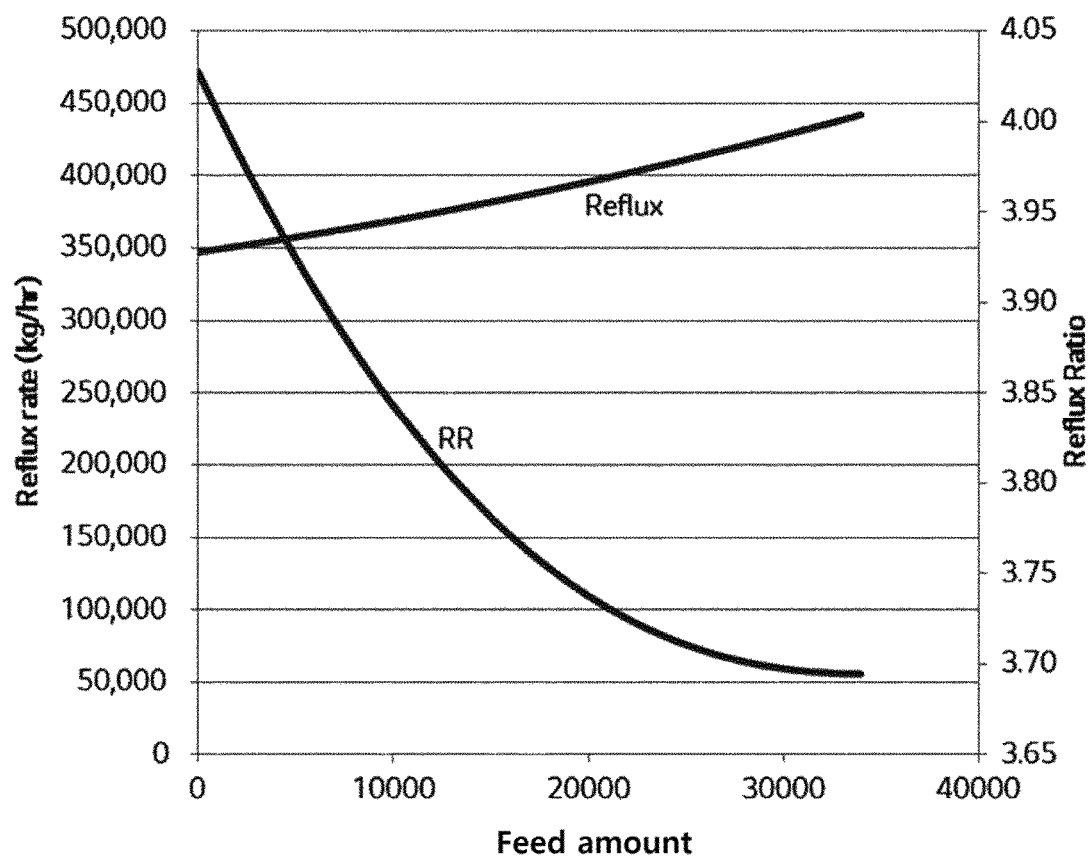

[Fig. 10]
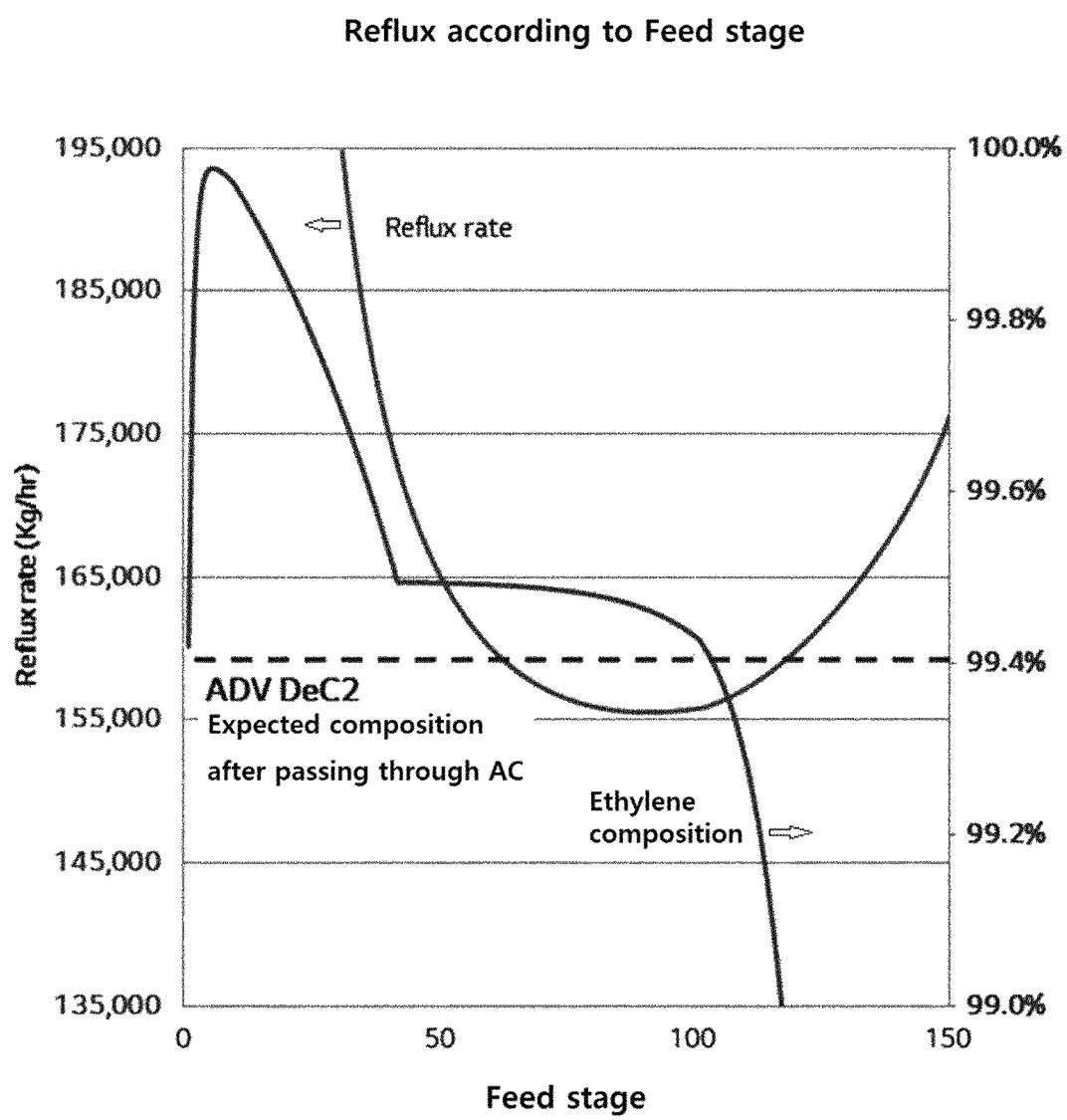

PROCESS AND APPARATUS FOR SEPARATING ETHYLENE

CROSS-REFERENCE TO RELATED APPLICATIONS

This application is the U.S. national phase of international Application No. PCT/KR2017/013234, filed on Nov. 21, 2017, and claims the benefit of priority to Korean Patent Application No. 10-2017-0071315, filed on Jun. 8, 2017, the entire disclosures of which are incorporated herein by reference.

BACKGROUND OF THE INVENTION

Field of the Invention

The present invention relates to a process for separating ethylene from a mixture comprising acetylene, ethane, ethylene and C3+, and more particularly to an ethylene separation process with improved process efficiency.

Background Art

Ethylene is a raw material for the manufacture of a wide range of chemical materials and is industrially produced by pyrolysis of hydrocarbons in a cracking furnace in which steam is present. The cracking furnace effluent stream containing various components is usually cleaned, dried to remove water, compressed and passed through an olefin recovery zone to separate ethylene from other light hydrocarbons such as ethane, propylene, propane and the like.

The order of separation of the mixture from the cracking furnace effluent can be started with a demethanizer column (DeC1), a deethanizer column (DeC2), or a depropanizer column (DeC3). For example, in a demethanizer column-first fractionation process, the effluent from the cracking furnace is cooled, extruded and then introduced into the demethanizer column to remove methane and light compounds. The bottom effluent of the demethanizer column is fed to the deethanizer column.

The deethanizer column separates the bottom effluent of the demethanizer column into a fraction containing C2 and light compounds flowing out of the overhead of the deethanizer column as steam and a fraction containing heavy compounds flowing out of the bottom of the deethanizer column. The bottom of the deethanizer column is treated to separate heavy compounds. Overhead C2 can be sent to an acetylene converter (AC converter) to convert acetylene into ethane and ethylene, or alternatively to an acetylene recovery unit to separate acetylene from ethane and ethylene. The effluent of reactor or recovery unit may be fed to a C2 separator (C2 splitter or C2 fractionator) and separated into ethylene and ethane.

There are many efforts to increase the ethylene production in the C2 separator. However, it has problems that there is often bottleneck due to limitations of existing equipment and that it is costly to change existing equipment. For example, in case that the acetylene converter is located upstream of the demethanizer column, the Advanced DeC2 process is used in which an effluent containing higher purity ethylene is supplied to the ethylene separator by providing a second deethanizer on the deethanizer column. However, this process has a problem in that it is difficult to be used because the acetylene converter cannot separate acetylene from the ethylene product in case that the acetylene converter is provided downstream of the deethanizer column.

SUMMARY OF THE INVENTION

An object of the present invention is to provide an ethylene separation process that can economically increase ethylene production without changing existing equipment in a process where an acetylene converter is located at the downstream of a deethanizer column.

In order to solve the above technical problem, the present invention provides a process for separating ethylene from a feed stream comprising an initial C2 stream comprising acetylene, ethane and ethylene and a C3 stream comprising propylene, the ethylene separation process comprising the steps of:

feeding the feed stream comprising the C2 stream and the C3 stream into a first deethanizer (DeC2) column to discharge a first C2 stream at the top and the C3 stream at the bottom of the first deethanizer column;

feeding a portion of the first C2 stream discharged at the top of the deethanizer column into a second deethanizer column to discharge a second C2 stream;

introducing a downstream of the second deethanizer column into the first deethanizer column again to serve as a reflux of the first deethanizer column;

supplying the second C2 stream into a first acetylene converter to convert acetylene contained in the second C2 stream into ethylene and discharge a first ethylene stream;

supplying the remaining stream of the first C2 stream discharged at the top of the deethanizer column into a second acetylene converter to convert acetylene contained in the first C2 stream into ethylene and discharge a second ethylene stream; and feeding the first ethylene stream and the second ethylene stream into an ethylene separation column to obtain ethylene.

According to one embodiment, the first ethylene stream may be fed into the middle of the ethylene separation column and the second ethylene stream may be fed into the bottom of the ethylene separation column.

According to one embodiment, the reflux ratio at the top of the first deethanizer column may be the same as the reflux ratio in the absence of the second deethanizer column.

According to one embodiment, the first C2 stream discharged at the top of the first deethanizer column may have an ethylene purity of 65 to 85 wt %.

According to one embodiment, the ethylene purity of the second C2 stream discharged from the second deethanizer column is 96 to 99 wt %, and the first ethylene stream after passing through the first acetylene converter may have an ethylene purity of 97 wt % or more.

According to one embodiment, the second ethylene stream after passing through the second acetylene converter may have an ethylene purity of 65 to 85 wt %.

According to one embodiment, the second deethanizer column may have a number of stages between 30 and 100.

According to one embodiment, the ethylene separation column may have a number of stages between 150 and 200, wherein the first ethylene stream may be fed into from stage 50 to stage 110 of the ethylene separation column and the second ethylene stream may be fed into 30 to 100 lower stage than the first ethylene stream.

According to one embodiment, the reflux ratio at the top of the ethylene separation column can be reduced compared to the reflux ratio in the absence of the second deethanizer column.

Effect of the Invention

The present invention provides an effect obtained by an ethylene preliminary separation process by adding a second deethanizer column and an acetylene converter on the conventional deethanizer column and enables to increase the ethylene production per unit volume by feeding the obtained first ethylene stream having a high purity of 99% or more into the middle of the ethylene separation column. The present invention can be applied to any facilities in which an acetylene converter is located downstream of a deethanizer column, so that the production of ethylene can be increased economically.

BRIEF DESCRIPTION OF THE DRAWINGS

FIG. 1 is a schematic process flow diagram of a conventional deethanization and ethylene separation process in which an acetylene converter is located downstream of a deethanizer column.
FIG. 2 is a schematic process flow diagram of an ethylene separation process according to the present invention.
FIG. 3 is a flowchart of the DeC2 process according to the conventional process (Base).
FIG. 4 is a flowchart of the process in which Advanced DeC2 process is added upstream of an ethylene separation column according to an embodiment of the present invention (Prefraction).
FIG. 5 compares the liquid load of the processes according to the comparative example (Base) and the example (Prefraction).
FIG. 6 is a process flow diagram of a process having a second deethanizer column (Advanced DeC2) on the deethanizer column according to an embodiment of the present invention.
FIG. 7 shows the ethylene purity according to the flow rate of the Advanced DeC2 stream in the process according to FIG. 6.
FIG. 8 is a flow diagram of a process for introducing 99 wt % ethylene into an ethylene separation column in accordance with an embodiment of the present invention.
FIG. 9 shows the reflux rate and the reflux ratio of an ethylene separation column according to the feeding amount of 99 wt % ethylene in the process according to FIG. 8.
FIG. 10 is a graph showing the reflux rate by the number of feed stage in the process according to the embodiment of the present invention and the expected ethylene composition after passing through the acetylene converter.

DETAILED DESCRIPTION

As used herein, "C #hydrocarbon" or "C #" (wherein #zis a positive integer) means to describe all hydrocarbons having #carbon atoms. In addition, the term "C #+ hydrocarbon" or "C #+" means to describe all hydrocarbon molecules having a carbon number greater than or equal to #. For example, the term "C3+ hydrocarbons" or "C3+" means to describe a mixture of hydrocarbons having three or more carbon atoms. Thus, the term "C3+ alkane" refers to an alkane having three or more carbon atoms. Thus, the term "C #minus hydrocarbon" or "C #minus" means to describe a mixture of hydrocarbons containing hydrogen with up to #carbon atoms. For example, the term "C2-" or "C2 minus" refers to a mixture of ethane, ethylene, acetylene, methane and hydrogen.

In the present invention, ethylene separation process is provided in that an acetylene converter is provided downstream of a deethanizer (DeC2), and a second deethanizer column (Advanced DeC2) and an acetylene converter are further disposed on the deethanizer column to increase ethylene production through the effect of prefractionator.

The ethylene separation process according to the present invention is a process for separating ethylene from a feed stream comprising a C2 stream comprising acetylene, ethane and ethylene and a C3 stream comprising propylene, the ethylene separation process comprising the steps of:

feeding the feed stream comprising the C2 stream and the C3 stream into a first deethanizer (DeC2) column to discharge a first C2 stream at the top and the C3 stream at the bottom of the first deethanizer column;

feeding a portion of the first C2 stream discharged at the top of the deethanizer column into a second deethanizer column to discharge a second C2 stream;

introducing a downstream discharge of the second deethanizer column into the first deethanizer column again to reflux the first deethanizer column;

supplying the second C2 stream into a first acetylene converter to convert acetylene contained in the second C2 stream into ethylene and discharge a first ethylene stream;

supplying the remaining stream of the first C2 stream discharged at the top of the deethanizer column into a second acetylene converter to convert acetylene contained in the first C2 stream into ethylene and discharge a second ethylene stream; and feeding the first ethylene stream and the second ethylene stream into an ethylene separation column to obtain ethylene.

In the present invention, a second deethanizer column is additionally provided downstream of the first deethanizer column to produce a high purity ethylene stream, and the high purity ethylene stream is introduced into the middle of the ethylene separation column to further improve ethylene production. The deethanization process using the second deethanizer column, which is additionally provided, serves as a prefraction step of the ethylene stream, so that the production amount of ethylene per unit volume can be increased as compared with the conventional ethylene separation process.

According to one embodiment, the first ethylene stream may be fed into the middle of the ethylene separation column and the second ethylene stream may be fed into the bottom of the ethylene separation column.

According to one embodiment, the reflux ratio at the top of the first deethanizer column may be the same as the reflux ratio in the absence of the second deethanizer column.

According to one embodiment, the first C2 stream discharged at the top of the first deethanizer column may have an ethylene purity of 65 to 85 wt %, preferably 80 to 85 wt %.

According to one embodiment, the ethylene purity of the second C2 stream discharged from the second deethanizer column is 96 to 99 wt %, and the first ethylene stream after passing through the first acetylene converter may have an ethylene purity of 97 wt % or more. The ethylene purity of the second C2 stream is much higher than that of the first C2 stream.

According to one embodiment, the second ethylene stream after passing through the second acetylene converter may have an ethylene purity of 65 to 85%.

According to one embodiment, the second deethanizer column may have a number of stages between 30 and 100, preferably 30 to 80, more preferably 30 to 60. With the above-described number of stages, the efficiency with the high purity first ethylene stream can be maximized.

According to one embodiment, the ethylene separation column may have a number of stages between 150 and 200, wherein the first ethylene stream may be fed into from stage 50 to stage 110 of the ethylene separation column, preferably stage 80 to stage 110, more preferably stage 90 to stage 105, and the second ethylene stream may be fed into 30 to 100 lower stage than the first ethylene stream. With the above-described number of stages, the efficiency with the high purity first ethylene stream can be maximized.

According to one embodiment, the reflux ratio at the top of the ethylene separation column can be reduced compared to the reflux ratio in the absence of the second deethanizer column. As a result, the rate of ethylene production per unit volume can be improved.

The acetylene converter allows to contact the acetylene contained in the C2 stream with hydrogen, resulting in conversion of the acetylene to ethylene. Therefore, the ethylene stream forms a lean acetylene stream or essentially free acetylene stream.

According to one embodiment, the feed stream may be a stream of product obtained from a depropanizer column, a demethanizer column, a debutanizer column or a stipper of the demethanizer column, a cracking furnace effluent, a catalytic reactor effluent, or a combination thereof.

The first deethanizer column, the second deethanizer column, and the ethylene separation column may be equipped with a condenser, and the condenser may condense and collect the separated ethylene stream.

The ethylene separation column as used herein includes a "rectifier", which means a fractionation distillation zone comprising a plurality of trays. This zone allows the vapor from the feed stream to contact with a relatively lean liquid in ethane, resulting in the upper ethylene stream lean of ethane and does not provide reboiling or stripping of ethylene from the liquid collected from the feed tray. The bottom of the ethylene separation column may be fed with a second ethylene stream having a relatively low purity of ethylene, if necessary, heated or cooled in a heat exchanger for feeding.

The present invention also provides an ethylene separation system for separating ethylene from a feed stream comprising a C2 stream comprising acetylene, ethane and ethylene, and a C3 stream comprising propylene.

The ethylene separation system according to the present invention comprises:
  a first deethanizer (DeC2) column into which a C2 stream and a C3 stream are fed and which discharges the C2 stream at the top and a C3 stream at the bottom;
  a second deethanizer (Advanced DeC2) column disposed on the first deethanizer column and for further removing ethane from a portion of the first C2 stream discharged from the first deethanizer column;
  a first acetylene converter for converting acetylene contained in the second C2 stream discharged from the second deethanizer column into ethylene to remove acetylene;
  a second acetylene converter for converting acetylene contained in the remaining first C2 stream other than the first C2 stream fed into the second deethanizer column into ethylene to remove acetylene; and
  an ethylene separation column into which the first ethylene stream and the second ethylene stream are fed to separate ethylene.

According to one embodiment, the high purity first ethylene stream discharged from the first acetylene converter may be fed into the middle of the ethylene separation column.

According to one embodiment, the low purity second ethylene stream discharged from the second acetylene converter may be fed into the bottom of the ethylene separation column. The second ethylene stream may be fed into 30 to 100 lower stage than the first ethylene stream. With the above-described number of stages, the efficiency with the high purity first ethylene stream can be maximized.

Hereinafter, examples of the present invention will be described in detail so that those skilled in the art can easily carry out the present invention. The present invention may, however, be embodied in many different forms and should not be construed as limited to the embodiments set forth herein.

Hereinafter, abbreviations and symbols mean the following.
  DA401: First deethanizer column
  DA412/1412: Ethylene separation column
  DA403: Demethanizer column Comparative Example 1 and Example 1

FIG. 3 and FIG. 4 show a conventional DeC2 process (comparative example) and Advanced DeC2 process (example) according to the present invention, respectively. The four numbers indicated in the stream in each figure represent the temperature (° C.), pressure (kg/cm$^2$G), flow rate (kg/hr) and gas fraction from top to bottom. The process operating conditions are as follows.
  Properties of Feed: 100% gas
  A number of stages of the first deethanizer column: 81 stages
  A number of stages of the second deethanizer column: 50 stages (Example only)
  A number of stages of the ethylene separation column: 215 stages (DA1412 100 stages/DA412 115 stages)
  Purity and feed stage of the first ethylene stream: 99%, stage 100 (Example only)
  Purity and feed stage of the second ethylene stream:
    Comparative example: 82%, stage 151
    Example: 80%, stage stage 151

The production, reflux, load of condenser and reboiler, and liquid load of ethylene separation column of the process according to the comparative example and the example, were compared in Table 1.

TABLE 1

| Item | Comparative Example (Base) | Example (PreFrac) |
|---|---|---|
| Total amount of feed | 59.1 ton/hr | 17.3 + 41.8 = 59.1 ton/hr |
| Production | 48.4 ton/hr | 50.7 ton/hr |
| Reflux | 174.3 ton/hr | 157.7 ton/hr |
| Load of condenser | 15.048 Gcal/hr | 13.508 Gcal/hr |
| DA412 liquid load | 133.5 ton/hr | 108.3 ton/hr |

As shown in Table 1, in case that the preliminary separation process using the second deethanizer column is included, it is noticeable that the liquid load is reduced, which is shown in more detail in FIG. 5. In the process according to the present invention, the liquid load in the range of stage 10 to stage 100 was reduced by 21.5 ton/hr, and the liquid load in the stage 101 or lower was also reduced by 25.2 ton/hr, resulting in additional production of 6 ton/hr of ethylene. In the process according to the present invention, the reflux ratio (RR) is decreased from 3.597 to 3.114.

In the process according to the present invention, the reflux rate is decreased by 18.4 ton/hr in total, the condenser duty is decreased by 1.9 Gcal/hr in total, and the reboiler duty is decreased by 2.02 Gcal/hr in total. It was confirmed that the energy required for the separation process was reduced by including the preliminary separation process using the second deethanizer column.

Example 2: Purity of Ethylene According to Feed Flow Rate

FIG. 7 shows the purity of ethylene according to the flow rate of the second deethanizer column, when operating under the operating condition shown in FIG. 6.

Since this process is for ethylene purity before passing through the acetylene converter, acetylene is present in the stream. As a result, the purity of ethylene shows a limit of 98.9%, and the composition is not changed until 17 ton/h of ethylene is discharged.

Example 3: Reflux and Reflux Ratio According to Feed Amount of High Purity Ethylene Stream In the above, it was confirmed that an ethylene stream of about 99% can be obtained via the preliminary fractionation using the second deethanizer column according to the present invention. Changes in reflux and reflux ratio of ethylene column separation column were measured according to the feed amount of 99% ethylene stream.

As shown in FIG. 8, 99% ethylene stream was directly fed to stage 40 of DA402 (ethylene separation column). Changes in Reflux and RR (Reflux ratio) were measured while varying the feed amount of ethylene stream. The results are shown in FIG. 9 and Table 2.

TABLE 2

| 99% C2− | Reflux | RR | Product | Cond Duty | Reb Duty |
|---|---|---|---|---|---|
| 0 | 347387 | 4.0275 | 86253 | −29.39 | 10.40 |
| 1000 | 349410.5 | 4.0053 | 87237.92 | −29.56 | 10.49 |
| 2000 | 351467.7 | 3.9839 | 88222.58 | −29.74 | 10.59 |
| 3000 | 353559.8 | 3.9634 | 89207.13 | −29.91 | 10.68 |
| 5000 | 357855 | 3.9249 | 91175.86 | −30.28 | 10.88 |
| 6000 | 380061.2 | 3.9069 | 92160.04 | −30.46 | 10.98 |
| 7000 | 362308.4 | 3.8898 | 93144.1 | −30.65 | 11.09 |
| 8000 | 364598.2 | 3.8734 | 94128.03 | −30.85 | 11.20 |
| 9000 | 366932.2 | 3.8579 | 95111.83 | −31.04 | 11.32 |
| 10000 | 369311.9 | 3.8432 | 96095.5 | −31.24 | 11.44 |
| 12000 | 374214.4 | 3.8161 | 98062.45 | −31.66 | 11.69 |
| 13000 | 376740.1 | 3.8037 | 99045.73 | −31.87 | 11.82 |
| 15000 | 381946.6 | 3.7812 | 101011.9 | −32.31 | 12.10 |
| 16000 | 384629.8 | 3.7711 | 101994.8 | −32.54 | 12.24 |
| 17000 | 387367.4 | 3.7617 | 102977.6 | −32.77 | 12.39 |
| 18000 | 390160.3 | 3.7530 | 103960.3 | −33.01 | 12.55 |
| 19000 | 393009 | 3.7450 | 104942.9 | −33.25 | 12.70 |
| 20000 | 395913.7 | 3.7377 | 105925.3 | −33.49 | 12.87 |
| 21000 | 398874.8 | 3.7310 | 106907.7 | −33.74 | 13.04 |
| 22000 | 401892 | 3.7250 | 107890 | −34.00 | 13.21 |
| 23000 | 404964.9 | 3.7196 | 108872.2 | −34.26 | 13.39 |
| 24000 | 408093 | 3.7149 | 109854.3 | −34.52 | 13.57 |
| 25000 | 411275.5 | 3.7107 | 110836.4 | −34.79 | 13.76 |

TABLE 2-continued

| 99% C2− | Reflux | RR | Product | Cond Duty | Reb Duty |
|---|---|---|---|---|---|
| 26000 | 414511.2 | 3.7070 | 111818.5 | −35.06 | 13.95 |
| 27000 | 417798.9 | 3.7039 | 112800.4 | −35.34 | 14.15 |
| 28000 | 421137.1 | 3.7012 | 113782.4 | −35.62 | 14.35 |
| 29000 | 424524.2 | 3.6991 | 114764.4 | −35.91 | 14.55 |
| 30000 | 427958.2 | 3.6974 | 115746.3 | −36.20 | 14.76 |
| 31000 | 431437.3 | 3.6961 | 116728.3 | −36.49 | 14.97 |
| 32000 | 434959.3 | 3.6952 | 117710.2 | −36.79 | 15.19 |
| 33000 | 438522.2 | 3.6946 | 118692.2 | −37.09 | 15.41 |
| 34000 | 442123.7 | 3.6944 | 119674.3 | −37.40 | 15.63 |

The results show that Reflux increases and RR decreases as the amount of high purity ethylene stream increases. It can be shown that Reflux increases in proportion to the feed amount and RR (=L/D) can be expressed as reflux/amount of product. As the reflux increases, the amount of product increases. RR was decreased as the amount of ethylene was increased, because the increment of the amount of product was greater than that of reflux.

Example 4: Effect According to Feed Stage of Ethylene Separation Column

In the step of feeding the first ethylene stream after passing through the first acetylene converter into the ethylene separation column, the effect according to the feed stage of ethylene separation column was examined. FIG. 10 shows the reflux and the reflux ratio according to the feed stage.

The composition of the ethylene stream before passing through the acetylene converter is 98.9%. The expected composition of the first ethylene feed stream after passing through the acetylene converter is 99.4% and it can be determined between 99.0% and 99.7% depending on the reaction of the acetylene converter.

Referring to the graph of FIG. 10, it can be seen that the feed stage of between 80 and 100 has the highest preliminary separation effect, considering the possibility that the composition of the ethylene stream can be higher than 99.4% and the pattern of reflux change. If the feed stage is higher than stage 80, the purity of the ethylene product to be produced with 99.96% at the top of the column may be adversely affected and if the feed stage is lower than stage 100, the possibility of ethylene leakage at the bottom of the column increases, which may lead to increased reflux and reduced production and lower energy efficiency.

While the present invention has been particularly shown and described with reference to figures and embodiments thereof, it will be understood by those of ordinary skill in the art that the scope of the present invention is not limited thereby and that various changes and modifications may be made therein. Therefore, the actual scope of the present invention will be defined by the appended claims and their equivalents.

What is claimed is:

1. A process for separating ethylene from a feed stream comprising an initial C2 stream comprising acetylene, ethane and ethylene and a C3 stream comprising propylene, the process comprising the steps of:
feeding the feed stream comprising the initial C2 stream and the C3 stream into a first deethanizer column to discharge a first C2 stream from a top of the first deethanizer column and the C3 stream from a bottom of the first deethanizer column;
feeding a portion of the first C2 stream discharged from the top of the first deethanizer column into a second deethanizer column and discharging a second C2 stream from a top of the second deethanizer column;

introducing a downstream discharge of the second deethanizer column into the first deethanizer column again to reflux the first deethanizer column;

supplying the second C2 stream into a first acetylene converter to convert acetylene contained in the second C2 stream into ethylene and discharging a first ethylene stream from the first acetylene converter;

supplying a remaining portion of the first C2 stream discharged from the top of the first deethanizer column to a second acetylene converter to convert acetylene contained in the remaining portion of the first C2 stream into ethylene and discharging a second ethylene stream from the second acetylene converter; and feeding the first ethylene stream and the second ethylene stream into an ethylene separation column to obtain ethylene.

2. The process according to claim 1, wherein the first ethylene stream is fed to a middle of the ethylene separation column and the second ethylene stream is fed to a bottom of the ethylene separation column.

3. The ethylene separation process according to claim 1, wherein the first C2 stream discharged from the top of the first deethanizer column has an ethylene purity of 65 wt % to 85 wt %.

4. The process according to claim 1, wherein an ethylene purity of the second C2 stream discharged from the second deethanizer column is 96 wt % to 99 wt %, and wherein an ethylene purity of the first ethylene stream after passing through the first acetylene converter is 97 wt % or more.

5. The process according to claim 1, wherein the second ethylene stream after passing through the second acetylene converter has an ethylene purity of 65 wt % to 85 wt %.

6. The process according to claim 1, wherein the second deethanizer column has a number of stages between 30 and 100.

7. The ethylene separation process according to claim 1, wherein the ethylene separation column has a number of stages between 150 and 200, wherein the first ethylene stream is fed to the ethylene separation column from stage 50 to stage 110 of the ethylene separation column, and wherein the second ethylene stream is fed to the ethylene separation column at a state that is 30 to 100 lower than the first ethylene stream.

* * * * *